United States Patent [19]

Bannochie et al.

[11] Patent Number: 4,966,674
[45] Date of Patent: Oct. 30, 1990

[54] CERIUM OXYCOMPOUND, STABLE ANODE FOR MOLTEN SALT ELECTROWINNING AND METHOD OF PRODUCTION

[75] Inventors: John G. Bannochie, Plymouth, Great Britain; Robert C. Sherriff, Ingelheim-am-Rhein, Fed. Rep. of Germany

[73] Assignee: MOLTECH Invent S. A., Luxembourg

[21] Appl. No.: 328,361

[22] PCT Filed: Aug. 19, 1987

[86] PCT No.: PCT/EP87/00471

§ 371 Date: Jun. 2, 1989

§ 102(e) Date: Jun. 2, 1989

[87] PCT Pub. No.: WO88/01312

PCT Pub. Date: Feb. 25, 1988

[30] Foreign Application Priority Data

Aug. 21, 1986 [EP] European Pat. Off. ........ 86810374.8

[51] Int. Cl.$^5$ ................................................ C25C 7/02
[52] U.S. Cl. ............................ 204/290 R; 204/291; 204/292; 423/263; 428/697; 428/699; 428/701
[58] Field of Search ............... 204/290 R, 290 F, 291, 204/292, 293, 67; 423/263; 428/421, 426, 457, 688, 689, 697, 701, 699

[56] References Cited

U.S. PATENT DOCUMENTS 3,578,580  5/1971  Hatting et al. .................. 204/243 R
4,614,569  9/1986  Duruz et al. ........................ 204/67

FOREIGN PATENT DOCUMENTS 0114085   7/1984  European Pat. Off. .
0203884  12/1986  European Pat. Off. .
0241083  10/1987  European Pat. Off. .
WO84/02724  7/1984  PCT Int'l Appl. .
2002739   2/1979  United Kingdom .

OTHER PUBLICATIONS

Chemical Abstracts, vol. 101, 1984, p. 303, Abstract #77684n.

*Primary Examiner*—John F. Niebling
*Assistant Examiner*—Kathryn Gorgos
*Attorney, Agent, or Firm*—John J. Freer

[57] ABSTRACT

The morphology of a coating of an oxyfluoride of cerium on a conductive substrate is improved by addition of tantalum, niobium and/or other pentavalent metals. Whereas a cerium oxufluoride coating shows cracks which may extend throughout the entire thickness of the coating, thus exposing finite portions of the substrate to corrosive attack, the pentavalent-doped coating has a substantially impervious structure. In addition to improvement of the coating morphology, the electrical conductivity is increased. The pentavalent-doped cerium oxyfluoride can be produced by electrodeposition or sintering. Coatings, substrates or bodies of this material may be employed as non-consumable anodes in molten aluminum electrowinning cells, as chemical sensors, or for corrosion protection and other applications.

9 Claims, 2 Drawing Sheets

CERIUM OXYCOMPOUND, STABLE ANODE FOR MOLTEN SALT ELECTROWINNING AND METHOD OF PRODUCTION

FIELD OF INVENTION

The invention relates to a material which is a coating material on electrically conductive substrates, a substrate material for an oxyfluoride coating or a bulk material, comprising an oxycompound such as an oxide or an oxyfluoride of cerium providing enhanced resistance against reducing as well as oxidizing environments and general chemical resistance up to temperatures of 1000° C. and higher.

The invention further relates to a method of manufacturing said coating.

Materials according to the present invention may be used to produce non-consumable anodes for electrowinning of metals by molten salt electrolysis, but there are also other possible applications, e.g. sensors for the chemical composition of fluids, such as oxygen sensors for gases or liquid metals. Further, the materials may be used as coating for corrosion protection at high temperature and generally for applications where electrical conductivity combined with chemical stability at high temperatures are desirable. Enhanced chemical stability at high temperatures is desired e.g. for protective coatings of heat exchangers exposed to corrosive environments.

BACKGROUND OF INVENTION

European Patent Application No. EP-A-0 114 085 discloses a dimensionally stable anode for an aluminum production cell comprising a conductive substrate of a ceramic, a metal or other materials which is coated with a layer of a fluorine-containing cerium oxycompound called "cerium oxyfluoride". The anode is essentially stable under conditions found in an aluminum production cell, provided a sufficient content of cerium species is maintained in the electrolyte.

The anode described in the above European patent application performs well in respect of dimensional stability. However, contamination of the produced aluminum by substrate components may occur under certain circumstances. As shown by microphotographs, the cerium-containing coating may have a structure with small imperfections such as pin-holes or cracks which produce small interstices between coated areas, allowing access of the electrolyte to the substrate. In such cases, the electrolyte may corrode the substrate leading to a limited but undesired contamination of the aluminum by substrate components.

The above reference also mentions that the protective coating on the anode may consist of the fluorine-containing cerium oxycompound and at least one other material which remains stable at the anode surface and forms a permanent component of the coating during operation. Materials which improve the electronic conductivity or electrocatalytic characteristics of the coating will be preferred.

European Patent Application EP-A-0 203 884 published on Dec. 3, 1986 proposed the addition of yttrium, lanthanum, praseodymium or other rare earth metals to the electrolyte in addition to cerium in order to obtain a cerium oxyfluoride coating which is doped with one of these metals and has an improved microstructure, substantially free of imperfections.

Other techniques have been proposed to preserve coatings eg of $TiB_2$ on a substrate which is immersed in a solution, by maintaining saturation amounts of titanium and boron in the solution, thus, providing an equilibrium between dissolution and re-deposition of these substances. These methods provide stabilization of the coatings rather than improvement of their morphology.

European Patent Application No. 87200587.1, as yet unpublished, discloses a method of producing a coating or a self-sustaining body comprising cerium oxyfluoride of the formula $CeO_xF_y$ where $x=1.5$ to $1.99$ and $y=0.01$ to $0.5$, by preparing a particulate starting material of the given composition and consolidating it into a shape or into a coating on a substrate. One method was to strip an electrolytically formed coating and then reconsolidate it. Another method was to provide a particulate starting material by reaction sintering.

SUMMARY OF THE INVENTION

It is one object of the present invention to provide a remedy for the above described contamination problem.

It is also an object of the invention to provide a material with improved electrical conductivity in order to decrease the required electrode potential when used as a protective coating or substrate for an aluminum electrowinning anode.

It is another object of the invention to provide a dimensionally stable anode for electrowinning a metal from a molten salt electrolyte containing an oxide of said metal, the anode having a coating which inhibits access of the electrolyte to the substrate.

It is a further object of the invention to provide a method of producing aluminum or other metals using a dimensionally stable anode comprising a coating wherein the formation of crevices and other deficiencies which eventually allow access of the electrolyte to the substrate is eliminated or at least substantially reduced.

It is a still further object of the invention to provide a simple technique for inhibiting contamination of the electrowon aluminum by substrate components by a method which is simple to apply and which is inexpensive.

Finally, it is an object of the invention to provide a fluorine-containing oxycompound of cerium with improved properties for general applications where one or more of the following properties—electronic and ionic conductivity and chemical stability against oxidizing as well as reducing environments at high and low temperatures—is desirable.

The above and other objects are met by a material which is a cerium oxycompound such a cerium oxyfluoride which further comprises at least one doping element selected from the group consisting of tantalum, niobium and other pentavalent metals, the concentration of the doping element(s) in the material being up to 10 w % with respect to Ce.

Materials according to the invention may comprise oxyfluorides of cerium and the doping element(s), wherein the concentration of the doping element(s) is between 0.1–5 w % of the cerium content.

The above material may be a coating on a substrate of a metal, an alloy, a conductive ceramic material or a cermet. The coating advantageously has a continuous coherent structure thereby providing a substantially impervious layer on the substrate. Preferred substrates for aluminum electrowinning are $SnO_2$ or $SnO_2$ based materials and alumina/aluminum-based cermets, in particular cermets comprising a ceramic phase of ceria and alumina and a metallic phase of a cerium-aluminum alloy. Such cermets are described in a copending patent application which is filed simultaneously herewith.

The coating may be produced in-situ by deposition of the constituents thereof onto the substrate immersed in an electrolyte containing said constituents in dissolved state, or ex-situ by sintering of a powder of the coating material or its precursor onto the substrate. When the mentioned dopants are added to the molten cryolite, they will deposit on the substrate only when cerium is also present in the molten cryolite and produces a cerium oxyfluoride deposit. The pentavalent metals alone would not deposit. Alternatively, a coating may be produced ex-situ by sintering a layer of the material on a substrate, or the material could be sintered as a self-sustaining body, or as one layer of a composite body, as described in more detail later.

The material according to the invention may serve in conjunction with a suitable substrate as an anode for electrowinning of metals by molten salt electrolysis, in particular for the production of aluminum from alumina dissolved in molten cryolite, or it may form the anode substrate.

However, other uses of these materials are intended and covered by the scope of the invention. Such other possible uses and applications of the material were already mentioned in the preamble of this specification and include chemical sensors, corrosion protection and chemically stable coatings for high and low temperatures.

In accordance with the invention, one method of producing a coating as described above is characterized by adding sufficient amounts of compounds of cerium and at least one pentavalent doping element such as tantalum or niobium to the electrolyte and passing electrical current with the coating and substrate under anodic polarization.

Good coating morphologies have been achieved in the Examples 1 and 2 with concentrations of the doping element(s) in the electrolyte in respect to cerium ranging from approximately 5 : 4 in Example 1 to 1 : 0.36 in Example 2. The anodic surface in these examples was 2cm$^2$ and the cerium concentration in the electrolyte was 1.2 w % in Example 1, and 1.8 w % in Example 2. It should be noted that the concentration of the doping element in the deposit does not significantly change with variations of its concentration in the electrolyte above a certain level, since a maximum concentration of the doping element in the coating is expected which corresponds to the thermodynamic solubility of the doping elements in the cerium oxyfluoride crystal lattice. On the other hand, however, the above values for the concentration of the doping additives in the melt may not be substantially decreased without affecting the coating composition and morphology. Depending on the differences of the doping elements and parameters of the coating process, the concentration of the doping elements in respect to cerium may vary from 0.1 : 1 to 100 : 1.

It is convenient for the bath chemistry if the compounds of the doping elements are oxides and/or fluorides.

Another aspect of the invention is the employment of the above described method of manufacture for the production of non-consumable anodes for electrowinning metal from its oxide dissolved in a molten salt electrolyte such as the production of aluminum by electrolysis of alumina dissolved in molten cryolite, which method comprises adding to the electrolyte prior to or during a preliminary period under special electrolysis operating conditions or during normal electrolysis a sufficient amount of compounds of cerium and at least one doping element selected from tantalum, niobium and other pentavalent metals. Continuing operation of the anode for producing metal may be assured by maintaining sufficient concentrations of cerium and, if necessary, the doping element(s) throughout normal electrolysis.

The entire or at least the initial production of the coating on the substrate may be carried out outside a molten salt electrowinning cell prior to the use of the anode in said cell. In this case, the coating is subsequently preserved by maintaining coating constituents (e.g. cerium) in the electrolyte at a concentration below their solubility limits. The equilibrium between dissolution and re-deposition of coating constituents does not require saturation concentrations thereof in the electrolyte when the substrate is anodically polarized. Thus, the coating may be entirely electroplated in a separate electrolysis cell or during preliminary or during normal electrolysis operating conditions within the electrowinning cell.

The choice and concentration of the doping elements from tantalum, niobium and other pentavalent metals may be carried out according to the intended use of the material, and will generally be governed by considerations of how the particular element influences the morphological, chemical and electrical properties of the material. Some doping elements may create enhanced ionic conductivity, which may be of interest for the sensor application, however, for its use as a coating for dimensionally stable aluminum electrowinning anodes electronic conductivity should prevail. In cases where the ionic conductivity is increased by the addition of such doping elements, the concentration thereof should not be too high in order to avoid undesired mass transfer through the coating.

The material according to the invention is composed of doped oxyfluoride which is extremely resistant to strong oxidizing as well as reducing environments and is chemically resistant to electrolytes such as found in a Hall-Heroult cell. The material is resistant to oxygen which is released in substantial amounts from the melt in the case of non-carbon anodes, and against fluorine which may be evolved from the cryolite under certain circumstances. The material is resistant against these gases since it is already composed of an oxyfluoride which is inert against further attack by fluorine and oxygen. Further, the cryolite in such cells contains a small concentration of dissolved metallic aluminum which is highly reducing, in particular, at the temperatures involved. The material is neither reduced by liquid aluminum in bulk nor aluminum dissolved in cryolite, since the oxides and fluorides of cerium and the doping elements are more stable than those of aluminum. The material also has enhanced conductivity which enables it to be used as anode substrate as well as the coating.

Figure 1:
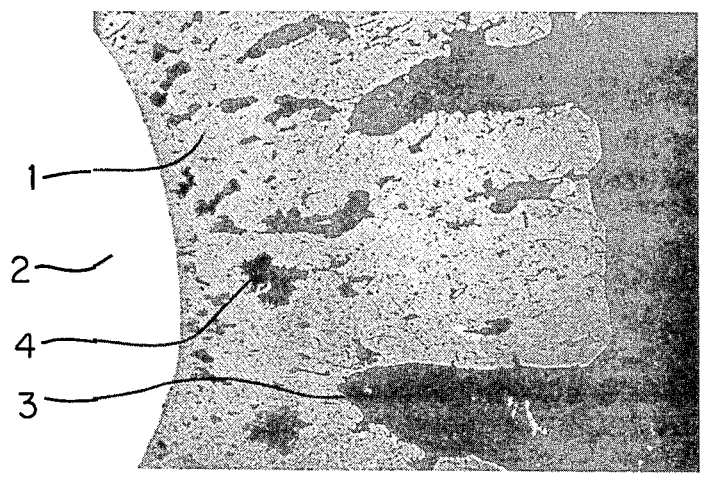
FIG. 1 shows a coating according to the prior art.

These figures will be discussed more particularly hereinafter in connection with the examples.

DETAILED DESCRIPTION OF THE INVENTION

The invention is now described in view of its application for dimensionally stable anodes for electrowinning of metals by molten salt electrolysis.

The dimensionally stable anodes over which the anodes of the present invention are an improvement are described in European Patent Application No. EP-A-0 114 085, this document being referred to such as fully incorporated herein.

As mentioned above, known anode coatings of cerium oxyfluoride lead to a small but undesired contamination of the aluminum by corrosion of the substrate to which the electrolyte finds limited access by small imperfections of the cerium-containing coating.

The present invention was based on the finding that the addition of small amounts of selected doping elements modifies the coating morphology in such beneficial manner that the coating is developed with a continuous coherent structure, providing a substantially impervious layer on the substrate, which virtually completely sheathes the substrate and prevents access of electrolyte. In addition, the doping increases the electrical conductivity, enabling use of the material also as an anode substrate layer or body.

The cerium oxyfluoride coating including these doping elements selected from tantalum, niobium and other pentavalent metals may be prefabricated outside the electrolysis cell and inserted therein once an impervious coating has been formed. Alternatively, the coating may be produced within the cell in three different ways: firstly during operation of the cell but under preliminary, modified operating conditions; secondly during an initial operation period under normal operation conditions of the cell; and thirdly during normal operation. In either case, a new, uncoated substrate is immersed into the electrolyte and controlled amounts of compounds such as oxides and/or fluorides of cerium and the doping elements are added to the electrolyte and maintained at a suitable concentration.

The production of a coating according to the present invention may be by electrodeposition of the cerium-oxyfluoride in a fused-salt bath of suitable composition, but the same doped materials can also be produced by direct reaction-sintering of a particulate precursor mixture. Reaction sintering can be used for the production of the material as a coating, as a substrate layer or as a bulk material. One method of making a composite body which will be described in detail below is slip casting followed by sintering.

IN-SITU PRODUCTION

A coating according to the present invention may be produced by deposition of a fluorine-containing cerium oxycompound on an anode substrate during electrolysis of a molten cryolite bath containing alumina, a suitable cerium compound such as $CeO_2$, $Ce_2O_3$ or $CeF_3$ and a compound of the doping element such as $Ta_2O_5$ or $Nb_2O_5$. When the substrate is positively polarized, the desired coating begins to grow until equilibrium between re-dissolution and deposition is obtained.

The mentioned doping elements, in particular their oxyfluorides, precipitate on anode substrates such as $SnO_2$ only in the presence of the cerium compounds and even then the doping elements precipitate onto the anode substrate at a rate which is substantially lower than could be expected according to their concentration in respect to the cerium content in the electrolyte. The doping elements ie. their oxyfluorides are completely dissolved in the solid cerium oxyfluoride phase of the coating. It may, therefore, be possible to keep the content of the doping elements at least in an inner region of the coating at its initial level, thus, maintaining the imperviousness in this region even without further doping elements being added to the electrolyte. Thereafter, only the concentration of cerium needs to be maintained.

Furthermore, it is self-evident that such coatings with pentavalent doping elements produced in-situ can be subjected to the stripping and reconsolidation procedure of EP 87200587.1 either to reform a coating, or to form a self-sustaining body.

A detailed description of the in-situ plating process may be found in Examples 1 and 2 below.

EX-SITU PRODUCTION

An alternative production method of a material according to the present invention is disclosed in EP 87200587.1 and relates to sintering or reaction-sintering of the coating onto a substrate or into a self-sustaining body. Such sintering process may be carried out by providing a powder of the initial starting materials comprising cerium oxide(s) and cerium fluorides and a desired amount of a compound of the doping element(s), and heating the mixture to a temperature at which a chemical reaction is initiated which leads to the formation of the desired cerium oxyfluoride doped with e.g. tantalum, niobium or other pentavalent elements.

A particulate precursor mixture of $CeO_2$, $Ce_2O_3$, $CeF_3$ and/or $NH_4F$ including a small amount of an oxide of tantalum, niobium or other pentavalent elements is prepared with the appropriate stoichiometry to yield the desired end composition within the considered range of the pentavalent-doped cerium-oxyfluoride. The reaction-sintering process may be carried out according to known procedures to obtain a generally high density end product. However, should it be desirable to obtain a porous end structure, volatile additives may be added to the starting material or the chemical composition of the starting material may be such that volatile reaction products are evolved during the reaction-sintering process. The above mentioned $NH_4F$ is an example of such a volatile component acting at the same time as fluorine source.

It has been found quite unexpectedly that the inclusion of a fluoride in a sintering mixture of cerium oxide and a pentavalent oxide acts as a sintering aid which produces a doped oxyfluoride material having sufficient density and conductivity to be used as a bulk component of a substrate for aluminum electrowinning. In other words, such sintered materials can not only be anode coatings but also, a substrate or substrate layer on which an anode coating of doped on undoped cerium oxyfluoride can be deposited. These bulk sintered bodies of doped oxyfluoride are also useful in other applications such as for gas sensors.

A detailed description of one sintering process is given in Example 3.

A further method of producing a composite body consisting of an outer layer of doped cerium oxyfluoride and an inner core of a conductive oxide ceramic or metal for use as an inert anode in aluminum electrolysis cells will now be described.

A composite body consisting of an outer shell or layer of cerium oxyfluoride doped with pentavalent metals and an inner substrate or core of a material with relatively low electrical resistivity can be produced using a slip-casting technique as described below.

While the outer shell of cerium oxyfluoride protects the core from direct attack by cryolite, the core must neverthless be of a material resistant to oxidizing and rather corrosive conditions at high temperatures. It should also not react chemically with the cerium oxyfluoride to form non-conductive compounds. Conductive oxides such as tin oxide, oxides of transition element metals and mixed oxides containing transition element metals are suitable. Examples of such materials are $CuO$, $Cu_2O$, $La_{0.95}Sr_{0.05}CoO_3$, $LaCoO_3$, $SrFeO_3$ and $ZrCrO_3$. Particularly advantageous are those materials whose components do not jeopardize the quality of the aluminum produced in the cell if present in small concentrations.

A mixture of $CeO_2$, $CeF_3$ and $Ta_2O_5$ to give a final product of the desired composition is comminuted to give a fine particle size and an intimate mixture of the components using a known method, for example ball-milling. The particle size of the mixture, thus, produced should be substantially below 20 micrometer. The mixture is then dispersed in an aqueous or non-aqueous medium to give a suspension or slip containing preferably greater than 30% by volume of solid by capillary attraction.

This slip is poured into a cylindrical porous mould closed at its bottom end. After a layer of the desired thickness has built up on the mold wall, the rest of the slip is poured out of the mold and, while the surface of the deposit is still wet, is replaced by a second slip, prepared in a similar manner to the first, but from the conductive material desired to be used as the core. The second deposit may be terminated after the desired thickness is reached by pouring the slip out of the mold, or allowed to build up to a solid body. A reservoir of slip may be provided if necessary above the mold to compensate for shrinkage while the deposit is formed.

Figure 4:
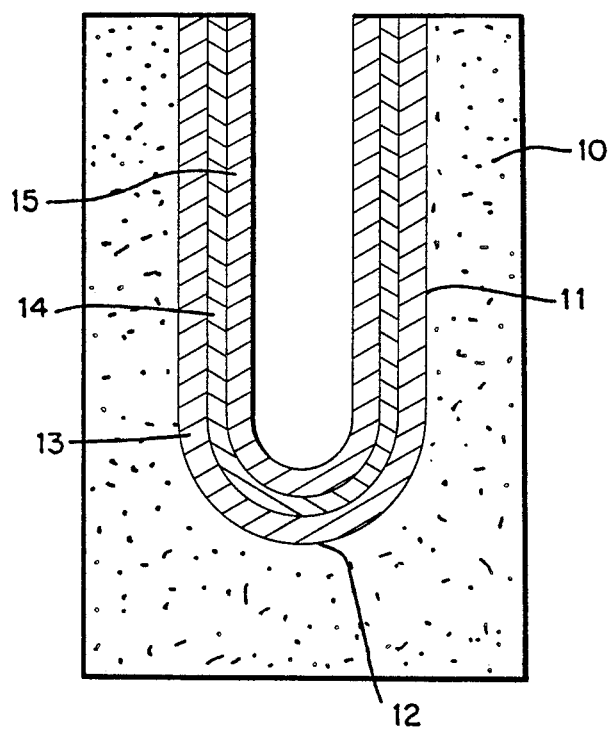
FIG. 4 is a schematic diagram showing a composite body during its production by slip casting.

If there is a significant difference in the thermal expansion or firing shrinkage of the two components used, it is advantageous to produce a body in which there is a more gradual transition from one material to the other, so that stresses caused by dimensional changes are reduced. In this case, one or more intermediate layers may be formed in the manner described using slips which contain mixtures of the two components in varying ratios. Such a composite body is shown in FIG. 4. Thus, another aspect of the invention consists of an aluminum electrowinning anode comprising a core of conductive ceramic, a substrate layer of cerium oxyfluoride doped with at least one pentavalent metal and at least one intermediate layer having a composition which is a mixture of the composition of the core and the substrate layer.

In all cases the body is consolidated by sintering at elevated temperatures after removal from the mould and drying.

Further details of this slip casting method are give in Example 4.

Operation and Maintenance of the Coating

The coating or layer as described above may be operated as an inert, dimensionally stable oxygen evolving anode in a molten salt aluminum electrowinning cell under constant conditions, where dissolution of the coating or layer is inhibited by maintaining suitable concentrations of coating constituents, e.g. cerium ions or cerium-containing ions and optionally, ions of the doping element, in the electrolyte.

Without being bound to any theory, it appears that the maintenance of the dimensional stability may involve an equilibrium between the dissolution rate of the coating in the electrolyte and the re-deposition rate of the dissolved constituents. Alternatively, the mere presence of coating constituents in the electrolyte may completely prevent the dissolution of the coating. The processes taking place at or near the anode surface are not completely known so far. It is believed that under anodic conditions, $Ce^{3+}$ ions are at least partially oxidized to $Ce^{4+}$ directly at the anode surface or by oxygen which had been discharged at the anode. The concentration of $Ce^{4+}$ is thereby practically increased to its solubility limit in the vicinity of the anodic surface and prevents the coating or layer from dissolving. It has been found that without anodic polarization the coating or layer slowly dissolves in the electrolyte.

Since a typical composition of the oxyfluoride matrix may be described by the formula $CeO_{1.9}F_{0.1}$, it is supposed that approximately 90% of the cerium is present in the form of $Ce^{4+}$ and only 10% as $Ce^{3+}$. This may explain why, as discussed above, anodic polarization of the anode surface, which increases the $Ce^{4+}$ concentration, may prevent the dissolution of the anodic surface.

The operating conditions may also be controlled intermittently, i.e. the anode is operated without replenishing the cerium in the electrolyte until a minimum coating thickness representing a safety limit is achieved, below which contamination of the bath and the product metal by corrosion of the substrate could occur. Then, the coating could be regrown by adding to the electrolyte the necessary compounds as mentioned above or the spent anodes can be withdrawn and replaced by new ones. The used anodes could then be recoated outside the cells for further use.

The choice of a particular doping element depends—as already mentioned—on the intended application of the material. In the case of materials for aluminum electrowinning anodes, it is relevant that oxyfluorides of the metals in question have not only electronic conductivity but also ionic conductivity as already mentioned before. Electronic conductivity is the preferred form, as ionic conductivity leads under particular conditions to the formation of a sub-layer between the substrate and the coating; this sub-layer being depleted of oxygen and composed of substantially pure fluorides of cerium and the doping elements. For this application, the dopant should, therefore, not substantially enhance the ionic conductivity over that of cerium oxyfluoride. Tantalum, niobium and some other pentavalent metals enhance the electronic conductivity by providing electrons in the conductivity band of the cerium oxyfluoride crystals. Other dopants which also increase the ionic conductivity may, however, be used in cases where only the improvement of the morphology is of interest and where electrical considerations are irrelevant, or where the material is not used under conditions which lead to the formation of the above mentioned intermediate layer.

EXAMPLES

The invention is described in the following by way of several examples illustrating the production and performance of materials according to the present invention by in-situ electroplating during electrolysis and by ex-situ sintering.

Example 1

A mixture of 333 g of an electrolyte comprising 87.5 w % natural cryolite, 8.8 w % alumina, 1.2 w % $CeF_3$ and 1.5 w % $Ta_2O_5$ were prepared. The electrolyte was heated to 970° C., and electrolysis was carried out for 8 hours passing current from a platinum anode of 3 mm diameter, providing 2 $cm^2$ active surface, to a $TiB_2$ cathode in the form of a disc of 15 mm diameter and 6.6 mm thick at an anodic current density of approx. 0.5A/$cm^2$. After the electrolysis, the anode was found to be coated with a 0.6 mm thick layer predominantly composed of cerium oxyfluoride of the formula $CeO_{1.9}F_{0.1}$.

The coating was investigated by energy dispersive electron probe microanalysis, and it was found that tantalum was present in an amount of approximately 0.7 mole %. The coating had a good interface with the substrate and a dense impervious structure. The coating is free from the aforementioned crevices and holes, so that no substrate portions are exposed to the electrolyte. Microcracks in the coating (visible in FIG. 2, discussed below) do not have any influence on the coating performance, since they are due to the sample preparation and would not occur in normal operation.

Example 2

To the same cryolite as used in Example 1 were added 1.8 w % $CeF_3$ and 0.5 w % $Ta_2O_5$. Electrolysis was carried out at 970° C. using an $SnO_2$ anode substrate of 4.5 $cm^2$ active surface area and a $TiB_2$ cathode such as used in Example 1, under an anodic current density of approx. 0.4A/$cm^2$. After 40 hours of electrolysis the anode was found to be coated with a 2.6 mm thick coating according to the present invention having satisfactory morphology and a good interface with the substrate.

Example 3

Figure 3:
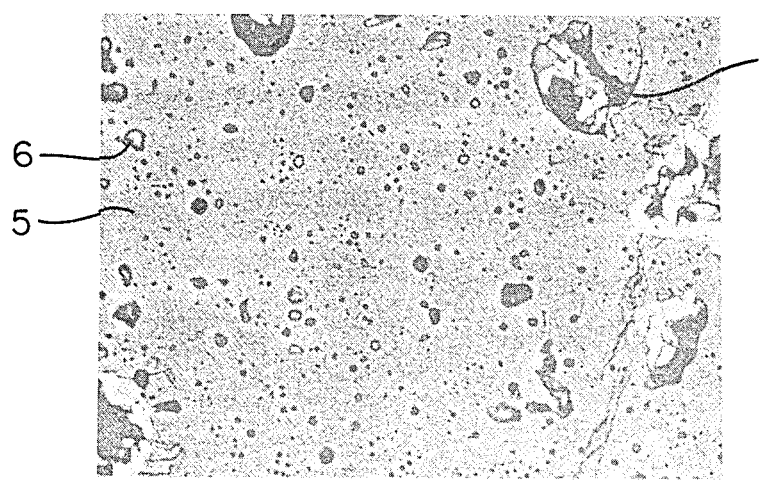
FIG. 3 shows the improved morphology of a body according to the invention incorporating doping elements.

A powder mixture comprising 99 mole % $CeO_2$ and 1 mole % $Ta_2O_5$ was isostatically pressed to a shape at a pressure of 25,000 psi (1,700 kg/$cm^2$), and sintered at 1500° C. in air for 4 hours. FIG. 3 is a microphotograph of the produced material showing a high density matrix including some small and occasional bigger voids. The overall density of this material was approximately 90-95%. The electrical resistivity of this material at 1000° C. was in the order of 3 ohm.cm compared to approximately 400 ohm.cm for pure $CeO_2$.

Example 4

A mixture of 93.3% $CeO_2$, 3.0% $Ta_2O_5$ and 3.7% $CeF_3$ by weight was comminuted in a ball mill and subsequently dispersed in water to give a concentrated suspension or "slip". This was drain cast in a plaster mould using known techniques to give a closed end tube with wall thickness of approximately 3 mm which, after drying, was consolidated by sintering at 1535° C. for two hours. The density of the body, thus produced was approximately 92% of theoretical, and it was found by microscopic examination t be essentially single-phased.

Using metallic silver (liquid at the operating temperature) as an internal electrical current feeder, this tube was anodically polarized in fused cryolite containing 10 w % alumina and 1.2 w % $CeF_3$ at a current density of 0.33 A/$cm^2$ for 24 h. The cell potential remained within the range 2.9-3.1 volts for the period of the test. On removal from the cell, the anode was found to be undamaged and had been coated with an additional approximately 1 mm thick layer of cerium oxyfluoride.

FIG. 1 is an illustration of a microphotograph of a coating according to the prior art with a magnification factor of 45. This coating 1 was obtained by immersion of an $SnO_2$ substrate 2 into a bath as described in Example 1 but without the addition of tantalum as dopant, only with 1.2% Ce. The current density was varied between 0 and 1 A/$cm^2$. The coating 1 has an average thickness of approximately 1.6 mm and covers the substrate 2 in a non-satisfactory manner. Large crevices 3 and voids 4 are visible in the coating which cause access of the electrolyte to the substrate.

Figure 2:
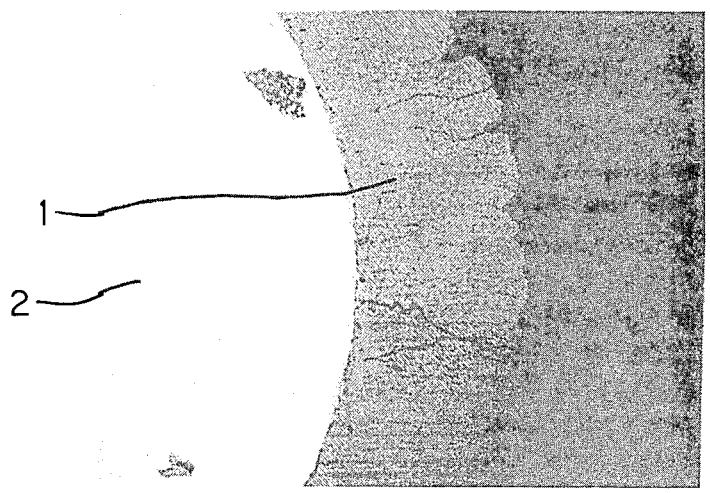
FIG. 2 illustrates a coating according to the present invention.

FIG. 2 is an illustration of a microphotograph with a magnification factor of 45 of a coating made according to Example 1 including $Ta_2O_5$ as the doping additive. As compared to FIG. 1, the coating 1 in FIG. 2, even though only 0.6 mm thick, is substantially improved in respect of its sealing effect for the substrate, i.e. its imperviousness. All large imperfections have disappeared, only some microcracks which are due to the sample preparation are visible. Such improved anode coatings are highly beneficial in that they reduce corrosion of the anode substrate by the electrolyte and the contamination of the metal produced.

FIG. 3 is an illustration of a microphotograph having a magnification factor of 300 of the sintered material according to Example 3 comprising 99 mole % $CeO_2$ and 1 mole % $Ta_2O_5$. A highly dense matrix 5 comprises some small pores 6 and occasional bigger voids 7.

FIG. 4 shows a composite material during its production by slip-casting as outlined above.

A cylindrical mold 10 of plaster of Paris has a cylindrical opening 11 with a hemispherical bottom 12. On the surface of this opening there is a first deposit 13 of $CeO_2$, $CeF_2$ and $Ta_2O_5$. Inside this there is an intermediate layer 14, and inside this there is an inner layer 15 of, for example, $CuO_2$, $La_{0.95} Sr_{0.05} CoO_3$ $LaCoO_3$, $SrFeO_3$ or $ZrCrO_3$. These layers are all deposited from slips, as described above. The intermediate layer 14 has a composition which is a mixture of the compositions of layers 13 and 15. Any desired number of intermediate layers 14 of graded composition can be deposited.

After removing the illustrated composite consisting of layers 13, 14 and 15 from the mold 10, the material is consolidated by sintering eg at about 1450° C.–1600° C. for 1–3 hours. The sintered body has a conductive ceramic core 15 coated with an outer layer 13 of tantalum-doped cerium oxyfluoride, joined by the intermediate layer 14. This body can be used with its core 15 as current feeder and its outer layer 13 as an anode substrate for aluminum electrowinning from alumina dissolved in molten cryolite with addition of cerium compounds and possibly dopants and other additives. Thus, the outer layer 15 is coated with cerium oxyfluoride doped with pentavalent elements such as tantalum and/or other rare earths such as yttrium, or without dopants.

We claim:

1. A material which is one or more of a coating material on electrically conductive substrates, or a substrate material for an oxyfluoride coating, or a bulk material, said material comprising an oxide or oxyfluoride of cerium providing enhanced resistance against reducing as well as oxidizing environments up to temperatures of 1000° C. and higher, said material further comprising at least one doping element selected from the group consisting of tantalum and niobium, the concentration of doping element in the coating being between 0.1–10 w % of the cerium.

2. The material of claim 1, wherein the concentration of doping element is between 0.1–5 w % of the cerium concentration.

3. The material of claim 1, coated on a substrate of a metal, an alloy, a ceramic material or a cermet.

4. The material of claim 3, wherein the substrate comprises $SnO_2$ or an aluminum/alumina-based cermet comprising ceria and cerium.

5. The material of claim 1, wherein the coating is produced by deposition of constituents thereof onto the substrate immersed in a molten salt electrolyte containing said constituents in dissolved state.

6. The material of claim 5, wherein the electrolyte is cryolite.

7. A dimensionally stable anode for electrowinning a metal from a molten salt electrolyte containing an oxide of said metal, the anode comprising the material according to claim 1, as an anode substrate or as coating.

8. A fluorine-containing oxycompound of cerium containing a pentavalent doping metal of one or more of tantalum or niobium in a concentration between 0.1–10 w % of the cerium.

9. An aluminum-electrowinning anode comprising a core of conductive ceramic, a substrate layer of cerium oxyfluoride doped with one or more of tantalum or niobium in a concentration between 0.1–10 w % of the cerium, and at least one intermediate layer having a composition which is a mixture of the compositions of the core and the substrate layer.

* * * * *